United States Patent

Bowling

[11] Patent Number: 6,116,776
[45] Date of Patent: Sep. 12, 2000

[54] METHOD AND APPARATUS FOR DETECTING IRREGULARITIES ON OR IN THE WALL OF A VESSEL

[75] Inventor: Michael Keith Bowling, Blackborough Cullompton, United Kingdom

[73] Assignee: Somerset Technical Laboratories Ltd., Somerset, United Kingdom

[21] Appl. No.: 08/945,974
[22] PCT Filed: Mar. 28, 1996
[86] PCT No.: PCT/GB96/00748
  § 371 Date: Sep. 29, 1997
  § 102(e) Date: Sep. 29, 1997
[87] PCT Pub. No.: WO96/30748
  PCT Pub. Date: Oct. 3, 1996

[30] Foreign Application Priority Data

Mar. 28, 1995 [GB] United Kingdom ............... 9506285
Sep. 27, 1995 [GB] United Kingdom ............... 9519672

[51] Int. Cl.[7] .................................................... G01M 3/00
[52] U.S. Cl. .................................................................. 374/4
[58] Field of Search ................... 374/4, 5, 6, 7, 374/110, 112, 116, 124

[56] References Cited

U.S. PATENT DOCUMENTS

| | | | |
|---|---|---|---|
| 3,761,713 | 9/1973 | Merrill | 374/124 |
| 4,343,182 | 8/1982 | Pompei | 374/124 |
| 4,768,158 | 8/1988 | Osanai | 374/5 |
| 4,983,836 | 1/1991 | Matoba et al. | 374/7 |
| 5,582,485 | 12/1996 | Lesniak | 374/124 |
| 5,834,661 | 11/1998 | Nonaka et al. | 374/5 |

FOREIGN PATENT DOCUMENTS

| | | |
|---|---|---|
| 0423085 | 4/1991 | European Pat. Off. . |
| 2182443 | 11/1973 | France . |
| 2453406 | 4/1979 | France . |
| 3713255 | 11/1988 | Germany . |
| 62-19269 | 8/1987 | Japan . |
| 2221997 | 2/1990 | United Kingdom . |
| 9726520 | 7/1997 | WIPO . |

OTHER PUBLICATIONS

Pulsed Infrared Imaging: A New NDT Methodology for Aboveground Storage Tanks, (Materials Evaluation), Jul. 1994, Maurice J. Bales et al., pp. 814–815.

Primary Examiner—G. Bradley Bennett
Attorney, Agent, or Firm—Galgano & Burke

[57] ABSTRACT

A method of detecting irregularities on or in the wall of a vessel by detecting localized spatial temperature differentials on the wall surface, comprising scanning the vessel surface with a thermal imaging camera and recording the position of the or each region for which the thermal image from the camera is indicative of such a temperature differential across the region. The spatial temperature differential may be formed by bacterial growth on the vessel surface; alternatively, it may be the result of defects in the vessel wall such as thin regions or pin holes or cracks. The detection of leaks through the vessel wall may be enhanced by applying a pressure differential or a temperature differential across the vessel wall; the testing for leaks may be performed with the vessel full or empty, and from the inside or the outside.

7 Claims, 4 Drawing Sheets

Air leakage into vacuum chamber 3 off cracks located in fillet welds outside milk evaporator Area 1 = Pinhole. Area 2 = Thinning Jacketed vessel!

Area 1 = Crack in jacketed silo

Leakage around door on milk spray dryer

METHOD AND APPARATUS FOR DETECTING IRREGULARITIES ON OR IN THE WALL OF A VESSEL

This invention relates to the detection of irregularities on or in the wall of a vessel, such as a food processing vessel for example, In one application, the invention is useful for detecting bacterial growth, and therefore of assessing the efficiency of cleaning of a food vessel, enabling contamination to be remedied. In another application of the invention, structural faults in the vessel wall may be detected for subsequent remedy, by identifying leaks or thin regions from the temperature distribution to which they give rise locally, The invention is useful in the detection of the presence of bacterial in any industrial plant and equipment. It is useful for the detection of leaks in vessels such as storage tanks processing equipment, and in refrigerated vehicles and rooms.

Vessels used to store or hold liquid products are prone to leaks, mainly caused by ageing. The impact of such leaks on the product varies according to the use of the vessel. In some cases serious contamination of the product can occur, which can lead to the product being discarded or recalled from retail outlets, either of which can be very costly.

In each case there is also a significant cost in diagnosing the leak, finding it, and rectifying it using traditional methods, Present preventative techniques often involve the shutting down of a plant or process, and the erection of expensive access equipment is often required. In addition, known techniques involving the use of dye penetrants to cover internal surfaces of the vessel can result in a leak being missed due to the dye being washed out of the flaw during removal of the excess dye.

One of the aims of the invention is to improve on the method of defect detection, including mitigating some or all of the disadvantages mentioned above.

Further, in any industry where freedom from bacteriological contamination is important, continual and sustained attention must be given to physical cleanliness and periodic sterilisation to ensure no traces of bacteria remain in preparation and receiving vessels, process plant, implements, transportable containers, and like instruments of activity.

Much industrial plant is of complex internal design, and although "CIP"—an industrial cleaning process—may be done methodically and thoroughly, a risk remains that the CIP cleaning agents have not been totally effective on all surfaces, corners and crevices of containers or implements. This problem has stimulated the formulation of this invention, which although usable on industrial plant after a cleaning operation to check the effectiveness of that operation, can usefully be employed to seek and find bacterial growth in any susceptible environment.

An aim of the present invention is to check for the presence of bacteria in, as a non-limiting example, a vessel in an industrial establishment after CIP work.

The invention provides a method as defined below. It also provides thermal imaging apparatus specifically set up to perform this method; and thermographs produced by the method of the invention, useful for locating and remedying the contaminant or the leak or other defect in or on the vessel wall.

In order that the invention may be better understood, examples will now be given with reference to the accompanying drawings, in which.

Figure 1:
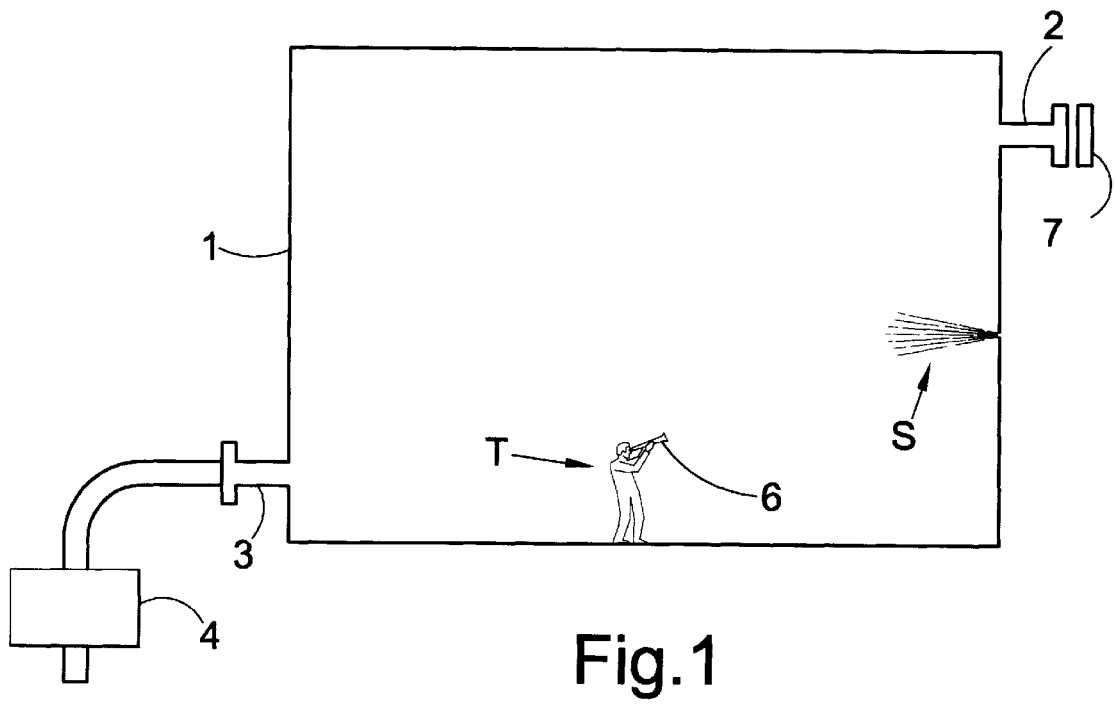
FIG. 1 is a diagrammatic sectional view of a non-jacketed food processing vessel undergoing testing in accordance with a preferred form of the invention.

Referring firstly to FIG. 1, a single-skinned food processing vessel 1 has a product inlet 2 and a product outlet 3. Any product contained in the vessel will be contaminated from the atmosphere, e.g. by air-borne bacteria, if any leaks are not found and remedied. To test the vessel for leaks the inlet 2 is sealed by a suitable closure 7 and a technician T enters the vessel 1, using breathing apparatus if necessary. A fan-type extractor 4 is coupled to the outlet 3 and another technician (not shown) working outside the vessel turns on the fan to draw air out of the product chamber and thereby create a pressure differential between the inside of the vessel and the external atmosphere.

When the pressure inside the vessel falls to less than $1.4 \times 10^4 Nm^{-2}$ (2 psi) the first technician T uses thermal imaging equipment 6 to scan the inner surface of the vessel wall, Any flaws in the wall will admit a stream of air S into the vessel, resulting in a localised temperature drop which will be rendered visible through the imaging equipment 6. The positions of any leaks are noted and the appropriate repair work can then be carried out before recommissioning the vessel.

Figure 2:
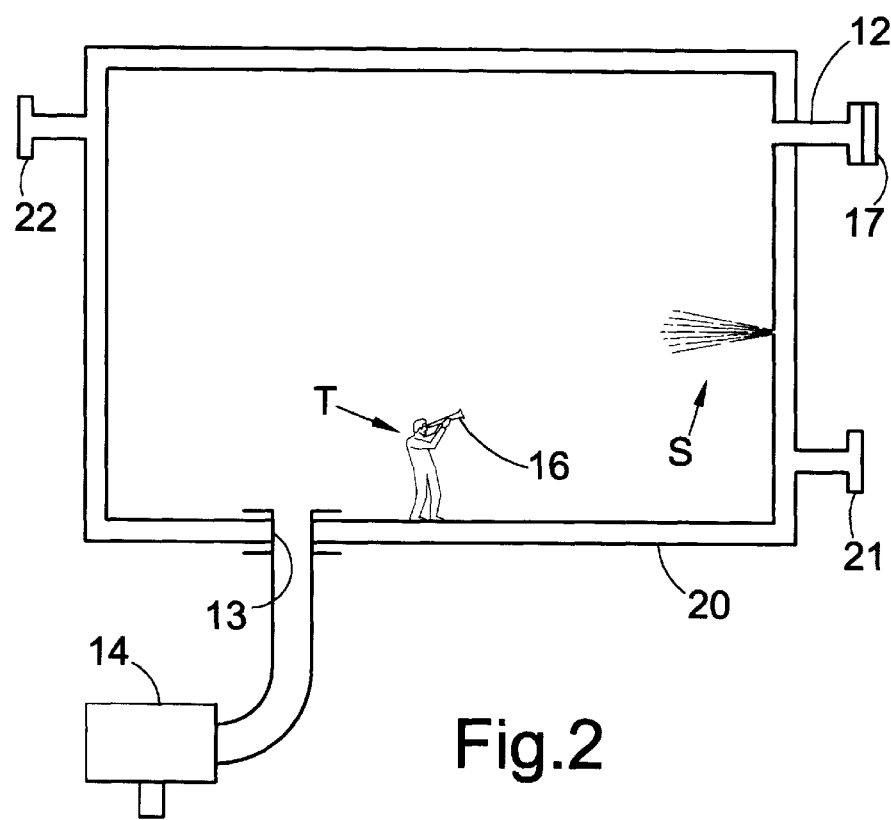
FIG. 2 and 3 are views corresponding to the view of FIG. 1, of a jacketed vessel undergoing two different forms of test in accordance with the invention.
Figure 3:
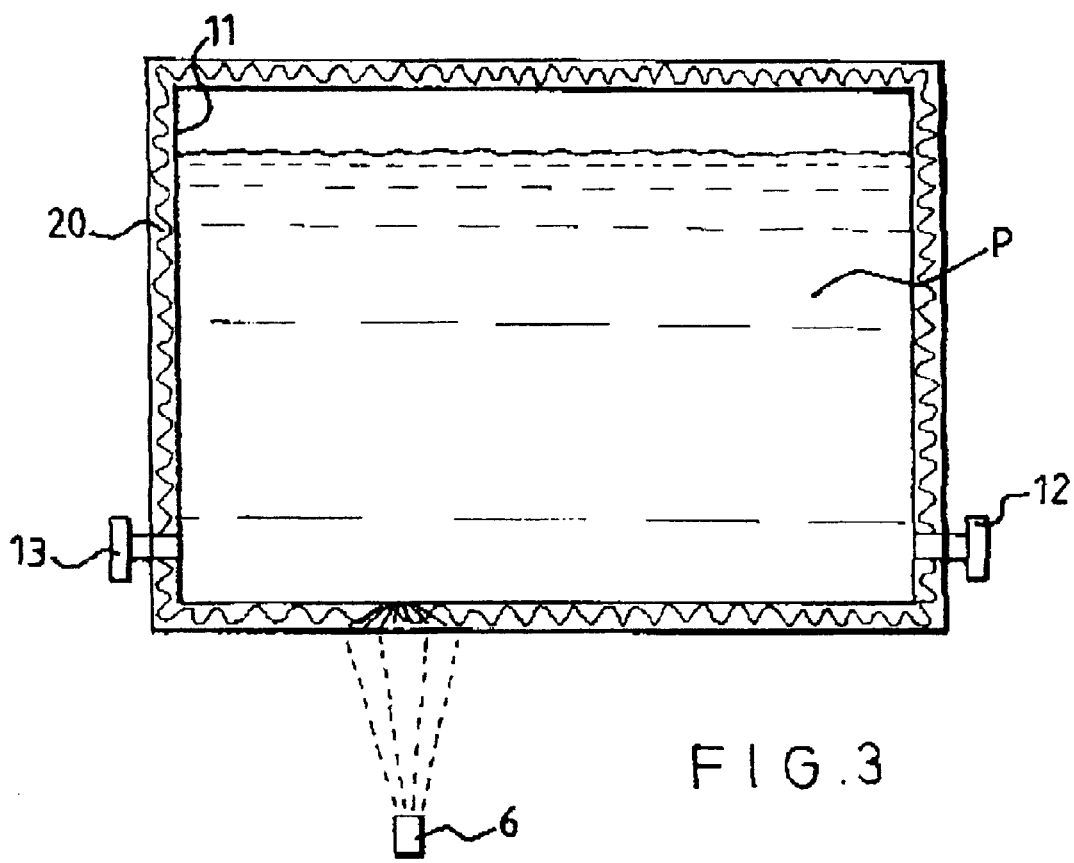

FIGS. 2 & 3 show another form of vessel 11 of the kind which is provided with a jacket 20 to contain either a heat-insulating material or a liquid cooling medium. If any leaks should occur through the inside wall of the vessel any product in the vessel (e.g. milk) will either be contaminated from the external atmosphere in the case of heat insulation, or from the cooling medium itself in the other case.

In FIG. 2, the illustrated vessel 11 has manway or access port 10 and product inlet and outlets 12 and 13 respectively. The jacket 20 has a coolant inlet and outlet 21 and 22 respectively. Any flaws in the wall of the vessel 11 will thus admit coolant (e.g. water) from the jacket 20 into the vessel, contaminating the contents. To test the vessel for leaks, product and coolant are first removed from the respective compartments. The coolant jacket 20 is then lightly pressurised, e.g. to around $1.4 \times 10^4 Nm^{-2}$ (2 psi), through the inlet 21 with the outlet 22 being sealed by a suitable closure, or vice versa. A technician enters the product compartment of the vessel through the manway 10, using breathing apparatus if necessary. The technician then views the inside surface of the vessel using suitable thermal imaging equipment. Any flaws (e.g. cracks and pinholes) in the vessel wall are rendered visible through the equipment due to changes in temperature of pressurised air entering the product chamber from the coolant jacket 20. Again, the position of any leaks can be mated for repair.

Any defects present in the wall can be confirmed and highlighted by spraying soapy water or the like onto the defect so that bubbles will appear as air enters the product chamber.

Special access equipment may be necessary, depending on the size of the vessel.

FIG. 3 illustrates an alternative leak detection method which method which can be used with insulated vessel where it is impractical to drain off the product. The product chamber is filled with product P at a temperature which is different (higher or lower) than the external temperature of the vessel. The product chamber may be pressurised, or the hydrostatic pressure of the product may be utilised to cause the product to penetrate any flaw in the wall of the product chamber. Due to the temperature difference between the leaking product and the external temperature the position of the leak can be detected using thermal imaging equipment 6.

Thus, the vessel can be examined for leaks in situ, without removal of the product.

Figure 4:
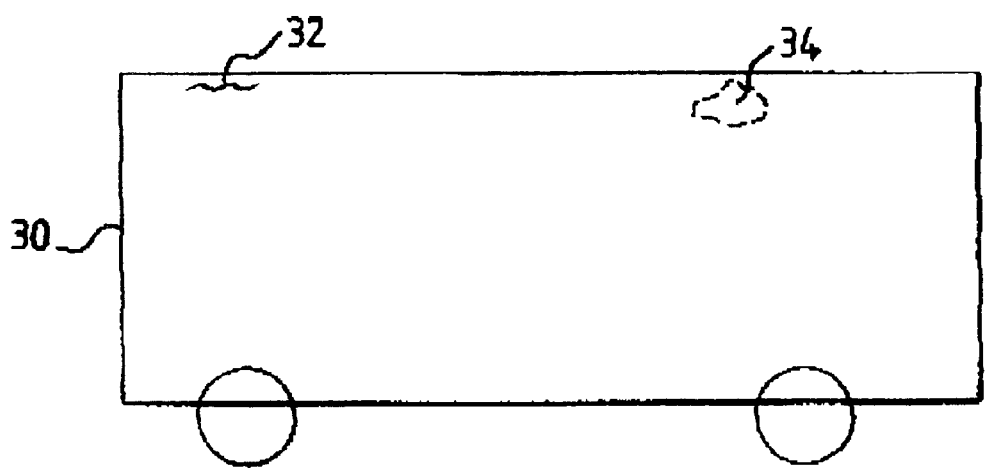
FIG. 4 is a diagrammatic sectional view of an insulated compartment of a vehicle, undergoing another form of the testing method of the invention.

FIG. 4 illustrates a similar method to that described in relation to FIG. 1, being used to check for leaks in a container such as a refrigerated room or refrigerated vehicle 30, of the kind which generally contains products requiring that a low temperature be maintained to ensure longer life, From time to time leaks may occur through the insulated wall of the room, causing an internal temperature rise and increased risk of product failure. When such vehicles are manufactured or repaired it is very difficult to test them for leaks using known testing methods.

To test the room or vehicle for leaks the inside temperature of the refrigerated compartment is reduced below external air temperature using the existing refrigeration equipment, and the internal surfaces are viewed with thermal imaging equipment. Any cracks 32 or breakdown of insulation 34 will be visible from inside the container using thermal imaging equipment, due to changes in surface temperature between the inside and outside of the container.

Since the process is quick and inexpensive to perform, the container can be checked for leaks at regular intervals allowing flaws to be detected before any serious contamination occurs.

The thermal imaging equipment used in the method of the invention may comprise a conventional infra-red thermal imaging camera and a computer-based disk storage system. Images from the camera are stored on disc so that they can then be improved by computer-aided enhancement techniques to reveal changes in surface temperatures. The resulting processed images are capable of assessment and analysis by computer.

In one preferred system, the surface of the vessel is scanned by an operator aiming a heat sensitive camera which sends its images to an on board computer with disc drive, equipped with a monitor and a video tape recorder. The images stored on the computer disc are then loaded into a second, more powerful computer equipped with an image enhancement program, to enable the temperature ranges to be raised and cross sectional temperature gradients to be plotted.

Although air is the most convenient gas to use it will be appreciated that other gases can be used, internally or externally.

Figure 5:
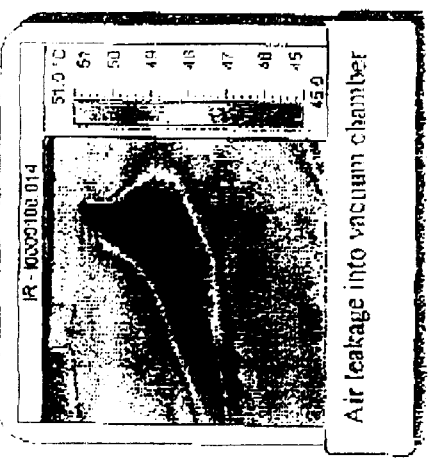
FIG. 5 is a half-tone reproduction in black and white of five coloured infra-red thermographs of different defects.
Figure 5:
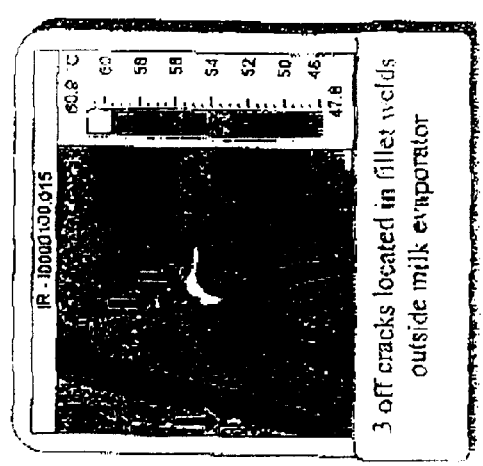
Figure 5:
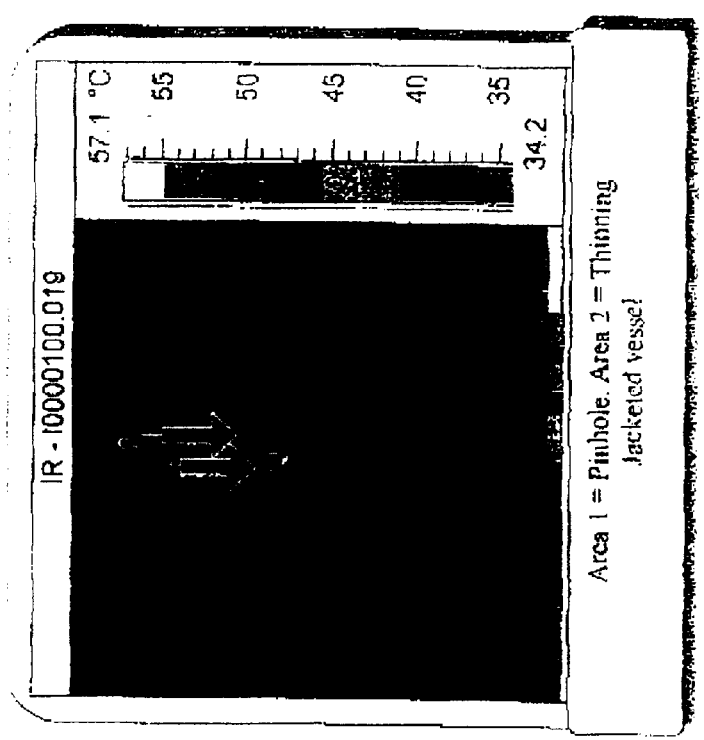
Figure 5:
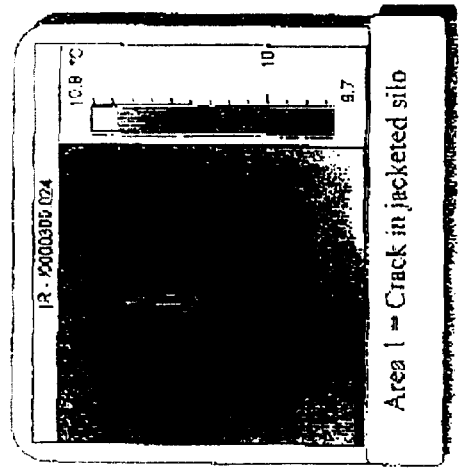
Figure 5:
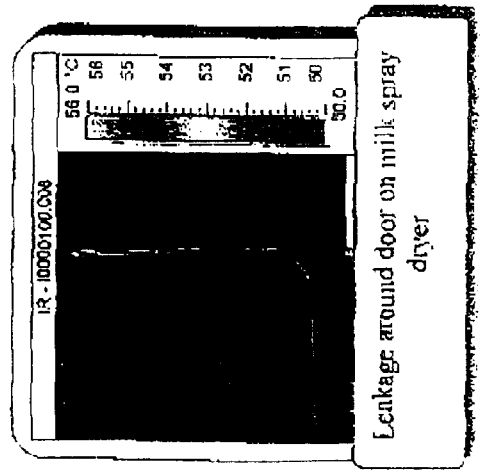
Figure 6:
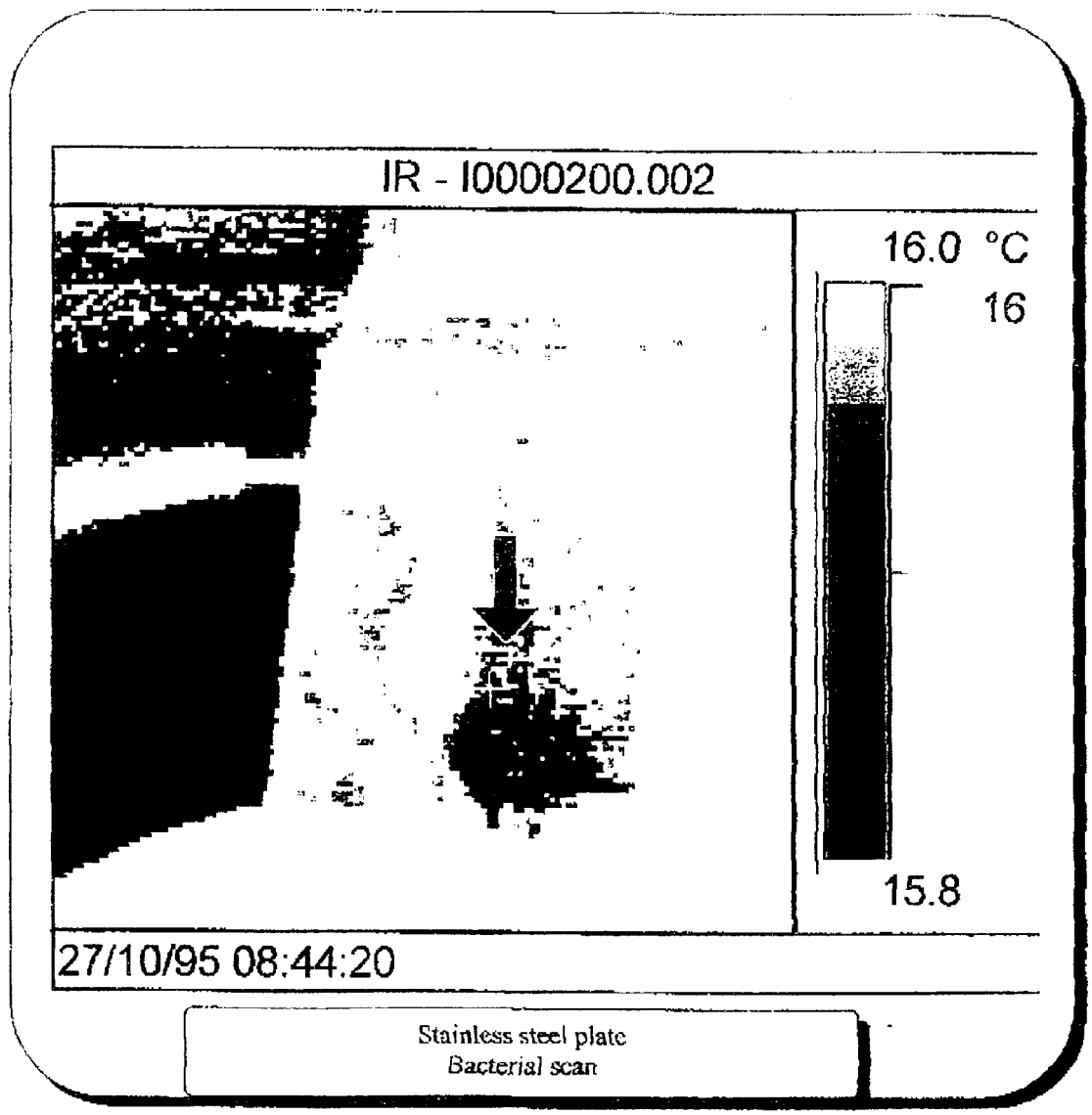
FIG. 6 is a half-tone reproduction in black and white of an infra-red thermograph of a stainless steel plate with bacterial growth on it.

The ability to detect a defect using thermal imaging in this way relies on the existence of a temperature differential between the inside and the outside surfaces of the vessel wall, in the case that there is no pressure difference, If there is a pressure difference, however, even if there is no temperature difference in bulk, the thermodynamic effect of a jet of fluid passing through a narrow "throttle" as it enters or leaves the vessel through the defect and the consequent fluid turbulence, give rise to a distinctive thermal pattern. For example, hot air spewing through a crack in the wall of a hot air dryer will be discernible by the use of a thermovision camera, as a thermal anomaly. The heat distribution on the colder side of the wall is portrayed on a video monitor, and a thermal anomaly is revealed as a patch of different colour on the monitor. The positional information of such thermal anomalies can be recorded on a synchronised video camera, operated concurrently with the thermovision camera, providing a thermal and visual presentation of the installation being scanned. An experienced operator, viewing the information presented, is able to differentiate between a hole in a containing wall and local thinning of the wall material. Anomalies can also be printed on a thermograph, to provide a permanent record; this preferably includes positional information for the target, obtained automatically from the video camera or entered manually e.g. from a keyboard. Such is the sensitivity of this process that defects can be detected beneath cladding and insulation. Examples of typical thermal images are shown in FIG. 5.

An example will now given of an alternative application for the invention.

Bacterial deposits are sources of radiant heat, and are therefor detectable by suitable means. If a sufficiently sensitive thermal detector is aimed at the surfaces, corners and crevices of any container or implement concerned, bacterial deposits will be detected through the capabilities of this invention and be capable of electronic portrayal on a suitable screen, through a suitable amplifier, In this way, the presence or absence of bacterial deposits can be confirmed.

In practice, as with the leak detection equipment described above, the thermal detector is installed in a mobile, self-contained hand-held camera gun which can be aimed as desired, an on which the thermal detection sensitivity can be varied to permit a detailed review of areas under surveillance. Thermal images can be stored on a floppy disc in an integral computer, for later detailed assessment through an enhancement program.

Just as the apparatus can detect a thermal anomaly due to the existence of a leak on the inside or outside of a containing wall, so can an anomaly due to the presence of living cells, eg bacteria. Bacteria prejudicial to the cleanliness of the good product concerned will be on the food side of any container, and this is where the chemical imaging camera is used, after regular operations to clean the inside, although the principle could apply to any similar situation. FIG. 7 shows a portion of the internal surface of a milk tanker which, after cleansing, was splashed with a small quantity of milk.

What is claimed is:

1. A method of detecting and locating fluid leaks through the wall of a food processing vessel comprising the steps of:
    introducing a fluid to one side of the food processing vessel wall, said vessel wall having a wall surface;
    scanning the vessel wall surface with a thermal imaging camera by aiming the camera to detect localized spatial temperature differentials on said wall surface; and
    continuously analyzing the thermal image for such a spatial temperature distribution that is indicative of a leak at a region, which leak is of sufficient magnitude to cause fluid movement through said vessel wall, and recording the position of said region.

2. A method as claimed in claim 1, further comprising the step of applying a pressure differential across said vessel wall in order to force said fluid movement through any leak in said vessel wall.

3. A method according to claim 1, further comprising the step of continuously analyzing the thermal image for a spatial temperature distribution indicative of the presence of localized bacterial growth on said wall surface.

4. A method as claimed in claim 2, wherein fluid is removed from within said vessel to establish said pressure differential.

5. A method as claimed in claim 1, wherein the fluid is air.

6. A method as claimed in claim 1, wherein there is substantially no temperature differential across said vessel wall.

7. A method according to claim 1, further comprising the step of applying a temperature differential across the vessel wall in order to enhance the localized spatial temperature differential adjacent to the region of the leak in said vessel wall.

* * * * *